US008087562B1

(12) United States Patent
Manoux et al.

(10) Patent No.: US 8,087,562 B1
(45) Date of Patent: Jan. 3, 2012

(54) ANVIL FOR SURGICAL INSTRUMENT

(75) Inventors: Philipe R. Manoux, San Francisco, CA (US); Bryan D. Knodel, Flagstaff, AZ (US); Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 92 days.

(21) Appl. No.: 12/489,355

(22) Filed: Jun. 22, 2009

(51) Int. Cl.
*A61B 17/068* (2006.01)

(52) U.S. Cl. ..................... 227/176.1; 227/19

(58) Field of Classification Search .............. 227/175.1, 227/176.1, 154, 155, 19, 77; 173/131
See application file for complete search history.

(56) References Cited

U.S. PATENT DOCUMENTS

| | | | |
|---|---|---|---|
| 3,581,551 A | 6/1971 | Wilkinson | |
| 3,650,453 A | 3/1972 | Smith, Jr. | |
| 3,899,914 A | 8/1975 | Akiyama | |
| 4,086,926 A | 5/1978 | Green et al. | |
| 4,228,895 A | 10/1980 | Larkin | |
| 4,475,679 A | 10/1984 | Fleury, Jr. | |
| 4,633,861 A | 1/1987 | Chow et al. | |
| 4,633,874 A * | 1/1987 | Chow et al. | 227/176.1 |
| 4,762,260 A | 8/1988 | Richards et al. | |
| 4,969,591 A | 11/1990 | Richards et al. | |
| 5,156,315 A | 10/1992 | Green et al. | |
| 5,192,288 A | 3/1993 | Thompson et al. | |
| 5,413,272 A | 5/1995 | Green et al. | |
| 5,476,206 A | 12/1995 | Green | |
| 5,505,363 A | 4/1996 | Green et al. | |
| 5,607,094 A * | 3/1997 | Clark et al. | 227/175.1 |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,833,695 A * | 11/1998 | Yoon | 606/139 |
| 5,839,639 A * | 11/1998 | Sauer et al. | 227/175.1 |
| 5,855,311 A | 1/1999 | Hamblin et al. | |
| 5,894,979 A | 4/1999 | Powell | |

(Continued)

FOREIGN PATENT DOCUMENTS

EP 1238634 9/1994

(Continued)

OTHER PUBLICATIONS

Gong, Shao W., "Perfectly flexible mechanism and integrated mechanism system design", *Mechanism and Machine Theory* 39 (2004), (Nov. 2004), 1155-1174.

(Continued)

*Primary Examiner* — Rinaldi Rada
*Assistant Examiner* — Andrew M Tecco
(74) *Attorney, Agent, or Firm* — Brian A. Schar

(57) ABSTRACT

An exemplary surgical apparatus may include an anvil with a body having a cavity defined therein, and at least one insert fixed within the cavity. Another exemplary surgical apparatus may include an anvil with an upper layer composed of a first material, and a lower layer composed of a second material different from the first material, where the lower layer is fixed to the upper layer. A method of manufacturing a surgical apparatus may include fabricating an anvil that includes a insert composed of a first material, the insert located within a cavity in a body composed of a second material, where the first material and the second material have different properties.

7 Claims, 3 Drawing Sheets

U.S. PATENT DOCUMENTS

| | | | |
|---|---|---|---|
| 5,918,791 A | 7/1999 | Sorrentino et al. | |
| 5,964,774 A | 10/1999 | McKean et al. | |
| 6,306,149 B1 | 10/2001 | Meade | |
| 6,391,038 B2 | 5/2002 | Vargas et al. | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,300,444 B1 * | 11/2007 | Nielsen et al. | 606/153 |
| 7,434,717 B2 * | 10/2008 | Shelton et al. | 227/176.1 |
| 7,543,729 B2 | 6/2009 | Ivanko | |
| 7,857,185 B2 * | 12/2010 | Swayze et al. | 227/175.2 |
| 7,857,186 B2 * | 12/2010 | Baxter et al. | 227/176.1 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 * | 4/2007 | Shelton et al. | 606/219 |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078805 A1 * | 4/2008 | Omaits et al. | 227/176.1 |
| 2009/0206140 A1 * | 8/2009 | Scheib et al. | 227/176.1 |
| 2010/0065606 A1 * | 3/2010 | Stopek | 227/176.1 |

FOREIGN PATENT DOCUMENTS

| | | |
|---|---|---|
| EP | 1464287 | 10/2004 |
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004), 265-272.

Kolios, Efrossini et al., "Microlaparoscopy", *J. Endourology* 18(9), (Nov. 2004), 811-817.

Steichen, Felicien M., et al., "Mechanical Sutures in Surgery", *Brit. J. Surg.* 60(3), (Mar. 1973), 191-197.

"Cardica Microcutter Implant Delivery Device 510(k), Cover Sheet, Table 10.1, "Substantial Equivalence Comparison," and Section 12, "Substantial Equivalence Discussion"".

* cited by examiner

ANVIL FOR SURGICAL INSTRUMENT

FIELD OF THE INVENTION

The invention generally relates to surgical staplers and stapling.

BACKGROUND

Referring to FIG. 1, a surgical stapler 2 typically includes a staple holder 4 and an anvil 6. The staple holder 4 and anvil 6 are configured to close together and clamp tissue therebetween. After clamping, the staple holder 4 deploys a plurality of staples into that tissue. A challenge faced by most surgical staplers 2 is beam deflection. When the surgical stapler 2 clamps tissue that is sufficiently thick and/or tough, the distal end of the anvil 6 may not close completely relative to the staple holder 4. Instead, the distal end of the anvil 6 may bend away from the staple holder 4, because more force is required to compress the tissue than to cause the distal end of the anvil 6 to bend. Many attempts have been made to solve this problem. Some surgical staplers 2 utilize an "I-beam" mechanism, where the upper and lower portions of the I-beam each slide in a corresponding channel in the staple holder 4 and anvil 6. However, the I-beam takes up space in the surgical stapler 2, limits cutting and stapling operations to being performed by motion in the distal direction, and adds to the part count. Other surgical staplers 2 have been proposed that utilize exotic, highly-stiff materials to reduce or eliminate beam deflection. Stiffness is the force required to produce a unit deflection of a structure, and is related to the elastic modulus of the material from which the structure is fabricated. Strength is the ability of a structure to resist loads. However, it is a truism of material science that stiff, high-modulus materials are not high-strength materials, with the result that such materials are not practical for fabrication of an anvil 6.

BRIEF DESCRIPTION OF THE DRAWINGS

The use of the same reference symbols in different figures indicates similar or identical items.

DETAILED DESCRIPTION

U.S. Patent Application Publication No. 2009/0065552, published on Mar. 12, 2009 (the "Endocutter Document"), is hereby incorporated by reference herein in its entirety. The Endocutter Document describes a surgical stapler 2 having a staple holder 4 and an anvil 6. The anvil 6 described in this document may be used in place of the anvil 6 described in the Endocutter Document, or in place of a convention anvil in any suitable surgical stapler 2.

Figure 1:
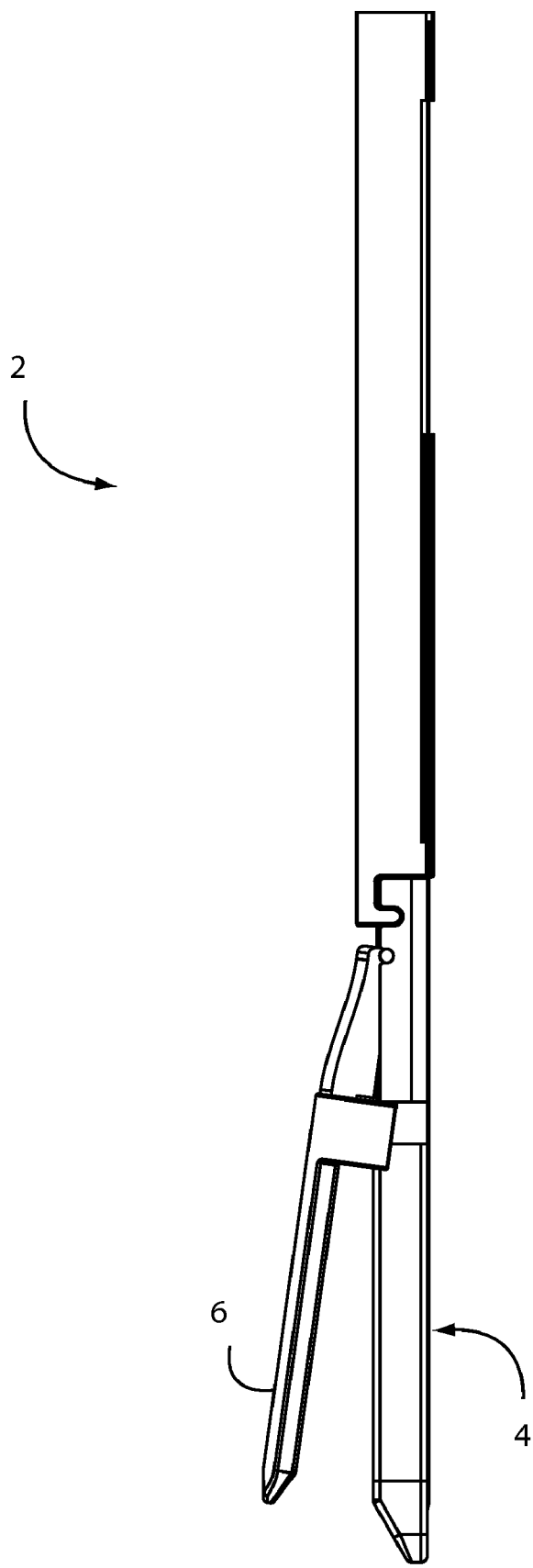
FIG. 1 is a side view of a surgical stapler.
Figure 2:
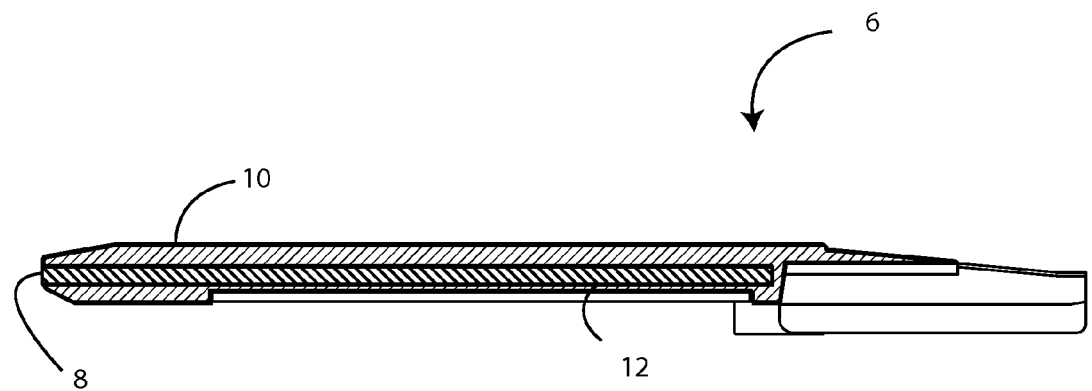
FIG. 2 is a cross-section side view of an exemplary anvil.
Figure 3:
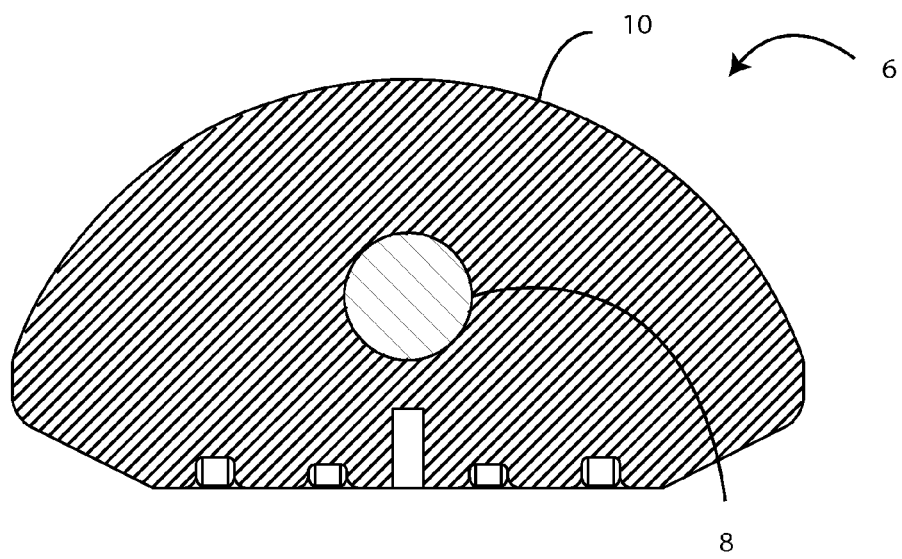
FIG. 3 is a cross-section end view of the anvil of FIG. 2.

Referring to FIGS. 2-3, an insert 8 is held within the body 10 of the anvil 6. That is, the body 10 is the part of the anvil 6 that receives the insert 8. The insert 8 may have any cross-sectional shape, such as circular, oval, rectangular, square, or any other suitable shape. The cross-sectional shape of the insert 8 may be constant, or may vary, along the length of that insert 8. The insert 8 may extend along part, or all, of the body 10 of the anvil 6. If the insert 8 extends along only part of the body 10 of the anvil 6, the insert 8 may be located at any suitable longitudinal position within the body 10 of the anvil 6. Advantageously, the insert 8 is stiffer than the body 10, and the body 10 is stronger than the insert 8. The insert 8 may be any high-modulus material, such as, for example, tungsten carbide. However, the insert 8 may be a different ceramic, metal, or any other suitable high-modulus material. The body 10 may be any high-strength material, such as, for example, 17-4 PH stainless steel. However, the body 10 may be ceramic, a different metal, or any other suitable high-strength material. Numerical analysis indicates that the use of a tungsten carbide insert 8 in conjunction with a 17-4 PH stainless steel body 10 results in an anvil 6 approximately three times stiffer than an anvil 6 composed of 17-4 PH stainless steel alone. The combination of a high-modulus insert 8 and a high-strength body 10 results in an anvil 6 that is stronger than the insert 8 alone could be, and stiffer than the body 10 alone could be. Alternately, the insert 8 may be a high-strength material, and the body 10 may be a high-modulus material. For the purposes of this document, "high-modulus" of the insert 8 or body 10 refers to a material having a higher modulus than the material from which the other is fabricated. Similarly, "high-strength" of the insert 8 or body 10 refers to a material having a higher strength than the material from which the other is fabricated.

The insert 8 and body 10 may be fabricated in any suitable manner. As one example, the insert 8 and the body 10 may be fabricated separately, and then the insert 8 may be placed into a corresponding cavity 12 within the body 10. The insert 8 may be held in place by a pressure or interference fit, by adhesive, by welding, by pinning, or by any other method, mechanism and/or structure. As another example, the body 10 may be insert-molded about the insert 8, or vice versa. Metal injection molding may be used to fabricate the body 10 about the insert 8, or to fabricate the insert 8 within the cavity 12 defined in the body 10. As another example, the body 10 may be cast about the insert 8. As another example, the insert 8 may be cast in place within the cavity 12.

Figure 4:
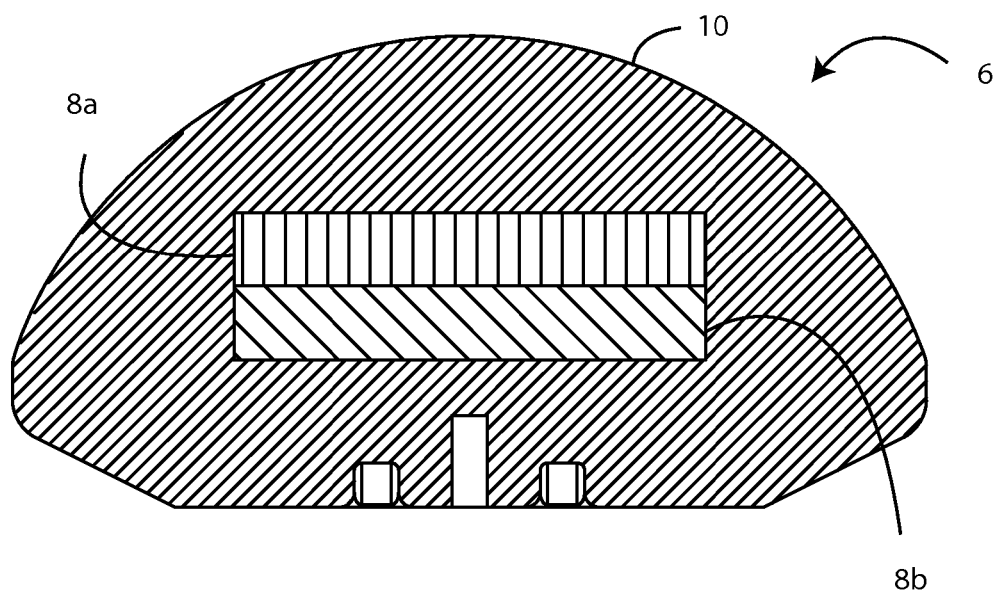
FIG. 4 is a cross-section end view of another exemplary anvil.

Referring also to FIG. 4, a different exemplary anvil 6 may include two or more inserts 8a, 8b held within the cavity in the body 10. The inserts 8a, 8b may have any suitable cross-sectional shape. For example, each insert 8a, 8b may have a generally rectangular cross-sectional shape, where the rectangle is wider than it is tall. The inserts 8a, 8b may have substantially the same cross-sectional area and shape as one another, or may be shaped and/or sized differently from one another. For example, one of the inserts 8a, 8b may be thicker than the other. The inserts 8a, 8b each may extend substantially the same length longitudinally, and/or may be located in substantially the same longitudinal position in the anvil 6. Alternately, at least one insert 8a, 8b may be shorter than another, and/or may be located in a different longitudinal position in the anvil 6. One insert 8a may be fabricated from a high-strength material, and another insert 8b may be fabricated from a high-modulus material; such inserts 8a, 8b may be stacked relative to each other in any suitable order. If so, the body 10 may be fabricated from plastic or other material, where the anvil 6 relies on the inserts 8a, 8b for both strength or stiffness, or may be fabricated from any other material, where the anvil 6 does not rely entirely on the inserts 8a, 8b to provide both strength and stiffness. Alternately, each insert 8a, 8b may be fabricated from a high-strength material and the body 10 may be fabricated from a high-modulus material, or vice versa.

Optionally, an upper insert 8a may be fabricated from a material that is stronger in compression than in tension, and a lower insert 8b may be fabricated from a material that is stronger in tension than compression. The upper insert 8a is further from the staple holder 4 than the lower insert 8b. The use of terms such as "upper", "lower" and "upwards" merely refers to the orientation of figures on the page for clarity and brevity, and does not limit the arrangement of the staple holder 4 and anvil 6, nor the orientation of the anvil 6 in use. In this way, as the anvil 6 and staple holder 4, the tendency of the distal end of the anvil 6 to bend upward away from the staple holder 4 is resisted both by the tensile strength of the lower insert 8b and the ability of the upper insert 8a to withstand compression. Typically, high modulus materials are stronger in compression than in tension, so in such a configuration the upper insert 8a may be fabricated from a high-modulus material and the lower insert 8b may be fabricated from a high-strength material.

Figure 5:
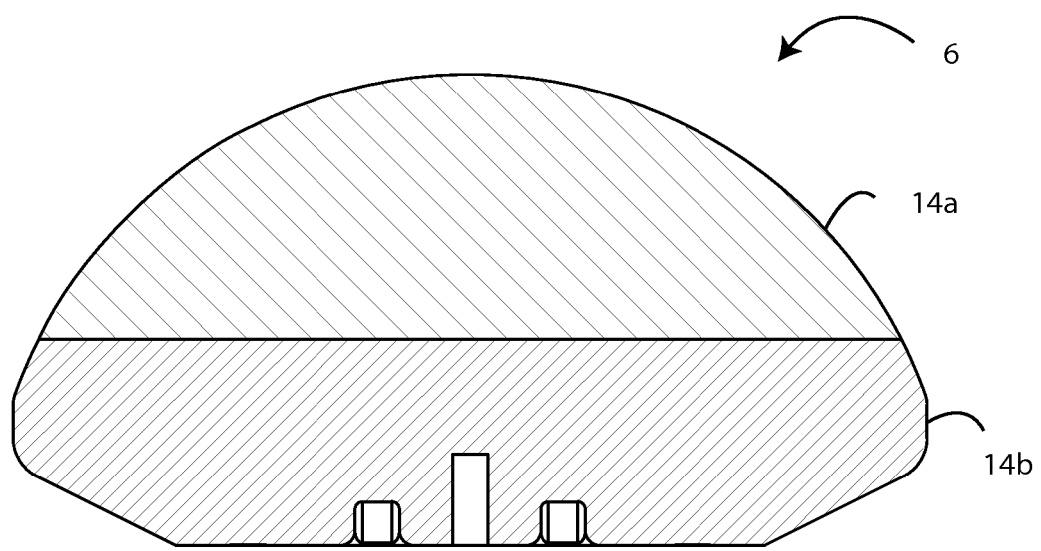
FIG. 5 is a cross-section end view of another exemplary anvil.

Referring to FIG. 5, a different exemplary anvil 6 may be fabricated from two separate, stacked layers 14a, 14b. In such a configuration, an insert 8 may not be utilized. However, an insert 8 may be provided in conjunction with the two layers 14a, 14b if desired; in such a configuration, the layers 14a, 14b may form the body 10 of the anvil 6, and the insert 8 is received into the cavity 12 of the body 10. The layers 14a, 14b may be fabricated from different materials and stacked in any order. As one example, an upper layer 14a may be fabricated from a high modulus material such as tungsten carbide, and a lower layer 14b may be fabricated from a high-strength material such as 17-4 PH stainless steel. As another example, the upper layer 14a may be fabricated from a high-strength material and the lower layer 14b may be fabricated from a high modulus material. The layers 14a, 14b may be fixed to one another to form a rigid anvil 6, and such fixation may be accomplished in any suitable manner, such as by adhesive, by welding, by pinning, by insert molding, or by metal injection molding. Optionally, one layer 14 may include one or more apertures (not shown) defined therein, and the other layer 14 may include one or more projections (not shown) configured to be received in those apertures. Such a configuration may facilitate the connection of the layers 14 to one another. The layers 14a, 14b each may extend along the entire length and width of the anvil 6. Alternately, at least one layer 14 may extend along less than the entire length and/or width of the anvil 6. If so, the other layer 14 may extend upward or downward to fill the remaining space. Alternately, one layer 14 may be composed of two or more separate pieces, each extending along less than all of the entire length and/or width of the anvil 6. In this way, the material properties of a particular layer 14 may be fine-tuned. The layers 14a, 14b may each be substantially the same height. Alternately, one layer 14 may be thicker than the other, depending on the desired stiffness and/or strength of the anvil 6 as a whole. As another example, the anvil 6 may be fabricated from three or more layers 14.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus for application of workpiece staples, comprising:
    a staple holder and an anvil, said anvil comprising a body having a longitudinal centerline and a cavity defined therein, wherein said body completely surrounds said cavity in at least one plane perpendicular to said longitudinal centerline, and wherein said body is configured to deform the workpiece staples upon contact therewith; and
    a plurality of inserts fixed within said cavity, wherein said inserts occupy substantially the entire cross-sectional area of said cavity at least at one location within said cavity, wherein the cross-section is perpendicular to the longitudinal centerline of said anvil; and wherein the elastic modulus of each said insert is different from that of at least one other said insert.

2. The surgical apparatus of claim 1, wherein at least one said insert is composed of a high-modulus material and said body is composed of a high-strength material.

3. The surgical apparatus of claim 1, wherein said body is composed of a high-modulus material and at least one said insert is composed of a high-strength material.

4. The surgical apparatus of claim 1, wherein at least two inserts, each having a generally rectangular cross-section, are stacked within said cavity.

5. The surgical apparatus of claim 4, wherein each said insert has substantially the same cross-sectional shape and area.

6. The surgical apparatus of claim 4, wherein one said insert is stronger than at least one other said insert in compression, and wherein at least one said insert is stronger than at least one other said insert in tension.

7. The surgical apparatus of claim 1, wherein said staple holder is pivotally connected to a proximal end of said anvil.

\* \* \* \* \*